(12) United States Patent
Dupont

(10) Patent No.: US 8,287,899 B2
(45) Date of Patent: Oct. 16, 2012

(54) PATCH FOR CUTANEOUS APPLICATION

(75) Inventor: Bertrand Dupont, Aix en Provence (FR)

(73) Assignee: DBV Technologies, Bagneux (FR)

( * ) Notice: Subject to any disclaimer, the term of this patent is extended or adjusted under 35 U.S.C. 154(b) by 490 days.

(21) Appl. No.: 12/527,407

(22) PCT Filed: Feb. 15, 2008

(86) PCT No.: PCT/FR2008/050252
§ 371 (c)(1),
(2), (4) Date: Aug. 14, 2009

(87) PCT Pub. No.: WO2008/104720
PCT Pub. Date: Sep. 4, 2008

(65) Prior Publication Data
US 2010/0119586 A1     May 13, 2010

(30) Foreign Application Priority Data

Feb. 15, 2007  (FR) ..................................... 07 53265

(51) Int. Cl.
*A61F 13/00* (2006.01)
(52) U.S. Cl. ........ 424/443; 424/402; 424/447; 424/448; 424/449

(58) Field of Classification Search ................... 424/402, 424/443, 447, 448, 449
See application file for complete search history.

(56) References Cited

U.S. PATENT DOCUMENTS

| 6,159,497 | A  | 12/2000 | Laprade et al. |
| 6,676,961 | B1 | 1/2004  | Lichter |

FOREIGN PATENT DOCUMENTS

| EP | 1 356 821 A2 | 10/2003 |
| JP | 003147394 U * | 12/2008 |
| WO | WO 02/074286 A1 | 9/2002 |
| WO | WO 2005/084255 A2 | 9/2005 |

OTHER PUBLICATIONS

Tamura, J. Medical adhesive patch has exfoliation simulation tape that is stuck onto peeling sheet with cutting lines at its center portion so that one end of tape is protruded out from peeling sheet, Dec. 25, 2008, JP 3147394 U, Derwent abstract 2009A56356.*

* cited by examiner

*Primary Examiner* — Gina C Yu
(74) *Attorney, Agent, or Firm* — Jones Day; Nicola A. Pisano; Jaime D. Choi

(57) ABSTRACT

The invention relates to a patch for cutaneous application of a substance, the patch comprising a substance designed to penetrate the epidermis, means for placing the substance in contact with the skin and a peelable cutaneous exfoliation film enabling exfoliation of the skin, after placing the patch, at the level of the contact zone between said substance and the skin.

19 Claims, 3 Drawing Sheets

PATCH FOR CUTANEOUS APPLICATION

CROSS-REFERENCE TO RELATED APPLICATIONS

This application is a national-stage filing under 35 U.S.C. §371 of International Patent Application No. PCT/FR2008/050252, filed on Feb. 15, 2008, the entire contents of which are incorporated by reference herein, which claims the benefit of French Patent Application No. FR0753265, filed on Feb. 15, 2007, the entire contents of which are incorporated by reference herein.

FIELD

The present invention relates in general to devices for epicutaneous or transcutaneous application of biologically active substances. The invention relates more particularly to transdermal patches or stamps designed to facilitate the cutaneous absorption of such substances for the purpose of vaccination.

RELATED ART

The human epidermis constitutes a barrier against external agents entering the body. The skin is not impervious, and is in fact permeable to a large number of substances with a varying degree of permeability.

Percutaneous absorption corresponds to the transfer of a substance through the skin from the external medium to the blood. This absorption is defined as the sum of two phenomena: penetration of molecules into the entire skin, followed by resorption by blood or lymphatic circulation from the papillary dermis then the deep dermis. The penetration step is physically passive diffusion through each structure of the tegument: the cornea layer, the Malpighi epidermis, the dermis and the cutaneous annexa. Once absorbed, the substance is distributed in the organism then, after being metabolised or not, it is eliminated. The steps succeeding percutaneous absorption are similar to those encountered for any other contamination path.

The cornea layer constitutes the most effective barrier against substance penetration: anatomically, the substance can penetrate in two ways: one through the intercellular spaces of the cornea layer and through the cornea cells themselves, and the other by means of cutaneous annexa. In the case of a vaccine, once the cornea layer is penetrated, the substance is in a position to encounter the immunologically competent cells and, in particular, the cells presenting antigens such as Langerhans cells, the role of which is primordial in the immunological reaction of the organism. Making initial passage of the antigen through the cornea layer easier is to make epicutaneous vaccination more efficacious. In the case of a patch designed to administer a molecule for systemic treatment, temporarily decrease the efficacy of the cornea layer as a barrier opens the way to transcutaneous administration of active ingredients having large molecular weights and, in general, improve the administration rate of the active ingredients.

The application EP 1 356 821 relates to the successive use of an adhesive film and a patch to have a vaccine penetrate epicutaneously. For this, a film having one face coated with an adhesive is applied to the skin. The adhesive has adhesion properties allowing it to remove part of the cornea layer (or stratum corneum) of the skin when the film is peeled. Once the film is peeled, a patch is applied to the part of the skin now uncovered. The patch has an adhesive surface and a surface coated with vaccine. The adhesive surface keeps the patch on the skin for a sufficient period to allow the epidermis to absorb the vaccine.

Such an administration process does have drawbacks. In fact, administration of the vaccine requires application of several devices in several steps. Also, positioning the patch is approximately relative to the zone where the adhesive film has been applied. Proper absorption of the vaccine is thus not guaranteed. Also, absent-mindedness can lead to forgetting previous application of the adhesive film. Therefore, the quantity of vaccine absorbed by the epidermis can be substantially reduced. The quantity actually absorbed by the epidermis is thus known relatively imprecisely.

SUMMARY

The invention aims to resolve one or more of these disadvantages. The object of the invention is thus a patch for cutaneous application of a substance, the patch comprising a substance intended to penetrate the epidermis, means for contacting the substance with the skin, and a peelable cutaneous exfoliation film enabling exfoliation of the skin, after the patch has been put in place, at the level of the contact zone between said substance and the skin.

According to a variant, the patch comprises:
- a support comprising at least one lower face having a first surface in contact with said substance and a second surface intended to make contact with the skin;
- optionally, removable means keeping the substance in contact with said first surface;
- the peelable cutaneous exfoliation film being solid with the support and comprising a lower face having an adhesive surface placed vertically to said substance; and
- means for keeping the second surface in contact with the skin when the exfoliation film has been peeled.

According to another variant, the second surface is adhesive and encloses the first surface.

According to another variant, the removable means for keeping the first surface in contact with the substance comprise a protective element interposed between the exfoliation film and the support, the protective element covering the first surface.

According to yet another variant, the means for keeping the second surface and the substance in contact with the skin comprise an adhesive coating the second surface, and the second surface has a part not covered by the protective element.

According to a variant, the patch comprises a peelable protective film covering and in contact with said non-covered part and with the lower face of the exfoliation film.

According to another variant, the patch comprises a prehension element projecting relative to the support, the prehension element being solid with the exfoliation film so as to delaminate it from the skin when it is handled.

According to another variant, the prehension part projects laterally relative to the support, to the side opposite the non-covered part by the protective element.

According to yet another variant, the prehension element is solid with the removable means, such that these removable means are removed when the prehension element is actuated.

According to a variant, the exfoliation film and the removable means are attached by respective first ends.

According to another variant, the prehension part is solid with a second end of the exfoliation film or removable means, this second end being opposite the first.

According to another variant, the removable means are formed by a film, and the prehension element is a film in contact with the film of the removable means and with the upper surface of the exfoliation film by means of faces partially coated with adhesive.

According to yet another variant, the removable means and the prehension element are constituted by a folded film.

According to a variant, the prehension element is folded back and attached removably on the upper surface of the support.

According to another variant, the prehension element projects perpendicularly to the lower face of the support.

According to another variant, the removable means and the prehension element are formed by an element in the form of a prism of triangular cross-section whereof the bases have prehension indents, whereof one lateral face covers the first surface, and whereof another lateral face is attached to at least one end of the exfoliation film.

According to yet another variant, the support and the removable means keep the substance in a volume of hermetic retention.

According to a variant, the substance has (or is in the form of) particles which are kept in contact with the first surface by electrostatic forces of Coulomb type or van der Waals forces. In a preferred mode, the first surface is endowed with electrostatic properties.

According to another variant, the adhesive power of the adhesive surface of the exfoliation film is calibrated as a function of the substance.

The invention also relates to the use of a patch such as defined hereinabove for the manufacture of a composition for delivering a substance to a patient.

According to a variant, this use is intended for the manufacture of a composition for vaccination of subjects, for desensitising subjects, or for delivering any active substance to a subject.

Another object of the invention relates to the use of a patch such as defined hereinabove for application of a substance to the skin, and/or for delivering a substance epicutaneously or transcutaneously to a subject, especially a mammal, in particular a human being (for example child or adult). The patch can especially be utilised for the vaccination of subjects, for desensitising subjects, or for delivering any active substance, such as especially biologically active and/or antigenic (poly) peptides, for example. The invention likewise relates to corresponding methods, comprising application of a patch of the invention to the skin of a subject, and removal of the exfoliation film.

The patch can thus be used for vaccination of subjects against any pathogen. Therefore, a particular object of the invention is a method of vaccination of a subject against a pathogen, comprising (i) the application of a patch according to the invention to the skin of a subject, the patch comprising a specific antigen of said pathogen, (ii) the removal of the exfoliation film and (iii) maintenance of the patch for a period of time allowing transfer of the antigen into the skin. The pathogen can be of a varied type (virus, bacteria, parasite, etc.) and the antigen is typically of polypeptidic or lipidic type.

The patch can likewise be utilised for desensitising subjects to allergens. So, a particular object of the invention is a method for desensitising a subject to an allergen, comprising (i) application of a patch according to the invention to the skin of a subject, the patch comprising a specific antigen of said allergen, (ii) removal of the exfoliation film and (iii) maintenance of the patch for a period of time allowing transfer of the antigen into the skin.

The patch can likewise be utilised for delivering any active substance. So, a particular object of the invention is a method of delivering an active substance to a subject, comprising (i) application of a patch according to the invention to the skin of a subject, the patch comprising said active substance, (ii) removal of the exfoliation film and (iii) maintenance of the patch for a period of time allowing transfer of the substance to the skin. The substance is typically polypeptidic in nature, such as a hormone, a cytokine, a growth factor, a trophic factor, etc.

The substance contained in the patch can be formulated in any vehicle or adapted excipient, and can be in solid (powder), liquid, etc. form.

BRIEF DESCRIPTION OF DRAWINGS

Other characteristics and advantages of the invention will emerge more clearly from the following description, by way of indication and non-limiting, in reference to the attached diagrams, in which.

DETAILED DESCRIPTION

The invention proposes a patch for the cutaneous application of a substance, the patch comprising a peelable cutaneous exfoliation film allowing exfoliation of the skin, after placing of the patch, at the level of the contact zone between said substance and the skin.

In terms of the invention, the term "exfoliation" or "abrasion" designates the removal of part at least of the surface of the superficial layer of the skin, and in particular of part at least of the cornea layer (or stratum corneum) of the skin. In this respect, the exfoliation film typically comprises an adhesive zone which makes contact with the skin. When it is removed (peeled), the exfoliation film causes abrasion of the surface of the skin. The exfoliation film can also comprise, typically on its adhesive zone which makes contact with the skin, micro-perforation means, thus adding to the removal of part of the surface of the cornea layer a micro-perforation action thereof, when the device is applied. Typically, exfoliation carried out in this way:

- removes, painlessly and at the site where transcutaneous or epicutaneous administration will take place, the superficial layer of cells of the cornea layer, generally dead cells, which make up the first barrier against penetration of substances, and/or
- constitutes a cleansed surface devoid of hairs, on which the patch can adhere over its entire adhesive surface, thus favouring occlusion and passage of the substance, and/or
- creates micro-perforations in the cornea layer, for example by fitting the film with perforating elements such as micro-needles.

In a particular embodiment, the patch comprises a support whereof part of the surface is covered by the substance intended to penetrate the epidermis and another part of the surface is intended to make contact with the skin. The peelable cutaneous exfoliation film is solid with the contact zone of the support and covers the surface covered with substance. On its lower face, it comprises an adhesive zone placed vertically to the substance. So, once the adhesive film is peeled, the substance is in contact of the skin at the exact placement where the skin has been exfoliated.

Figure 1:
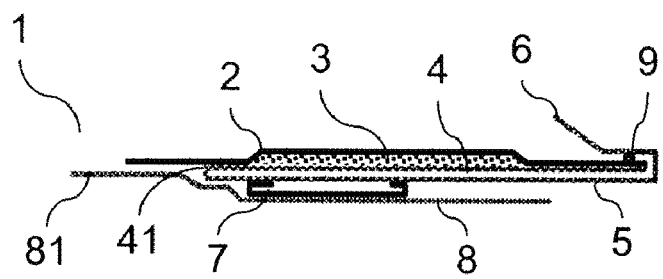
FIG. 1 is a sectional view of a first embodiment of a patch according to the invention.
Figure 2:
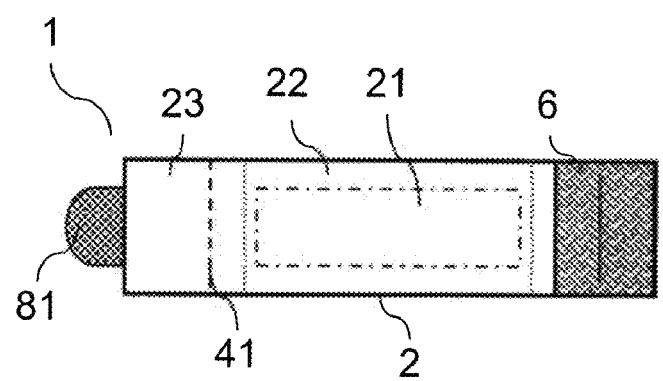
FIG. 2 is a plan view of the patch of FIG. 1.
Figure 3:
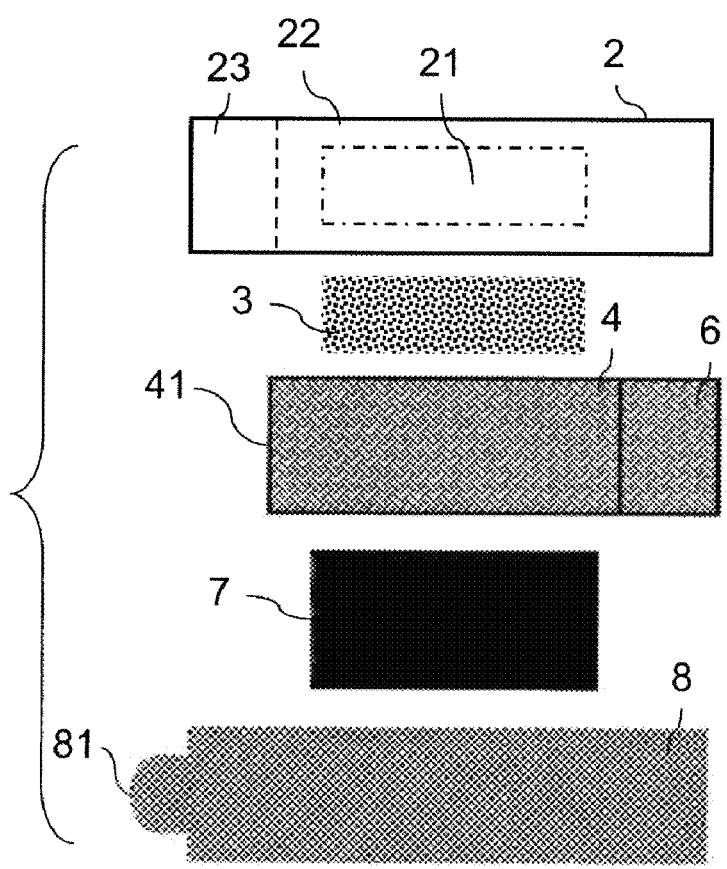
FIG. 3 is a plan view of each of the elements of the patch of FIGS. 2 and 3.

FIGS. 1 to 3 illustrate a first embodiment of the invention. The patch 1 comprises a support 2, made for example in the form of a film. The support 2 has a lower face having a first surface 21 intended to be kept in contact with a substance 3 and a second surface 22 intended to be applied to the skin. The substance 3 is intended to be applied to the skin. The surface 21 is situated in an indent of the support 2. The surface 22 is adhesive and encloses the surface 21. The adhesive surface 22 keeps the substance 3 in contact with the skin during application of the patch.

A film 4 covers the substance 3 and keeps it in contact with the surface 21. The film 4 forms a retention volume of the substance 3 with the surface 21. The retention volume formed is advantageously hermetic. In a manner known per se, the film 4 is fixed removably to the support 2. The film 4 is folded at the level of an end 41. A fold 5 extends from the end 41 of the film 4. The fold 5 is extended into a prehension element 6. The prehension element 6 is folded onto the upper face of the support 2. The prehension element 6 is kept folded removably by an adhesive point 9, such that a user can break this adhesive to handle the prehension element 6. The element 6 projects relative to the support 2, so as to ensure easy handling for the user. The film 4 does not cover part 23 of the adhesive surface 22. The utility of this adhesive part 23 will be detailed hereinbelow.

A peelable film 7 is attached to the fold 5 by any appropriate means (adhesion, welding . . . ) by its end closest to the adhesive part 23. This peelable film 7 is intended to perform cutaneous exfoliation. The film 7 is as such provided with a lower face having an adhesive surface. Exfoliation aims especially to remove part of the cornea layer to benefit transcutaneous penetration of the substance 3. This adhesive surface is placed vertically to the substance 3. Accordingly, the substance 3 will be applied exactly to the placement of the skin which will have been exfoliated during peeling of the film 7.

A peelable protective film 8 covers the adhesive part 23 and the lower face of the film 7, to prevent dust from settling on top. The peelable film 8 can be made from any adequate material having weak adherence to facilitate its peeling, such as for example paper or polymer (polyester, polyethylene, ethylene/vinyl acetate), optionally covered by a layer of silicon. The peelable film 8 also has a prehension zone 81, protruding relative to the surface 23 of the support 2. This prehension zone 81 makes it easy for a user to peel the film 8.

When a user wants to apply the patch 1, he proceeds as follows: he peels the film 8, applies the adhesive of the exfoliating film 7 to the skin and places the adhesive surface 23 onto the skin. The adhesive surface 23 then guarantees proper positioning of the patch on the skin. After having broken the adhesive point 9, the user exerts traction on the prehension element 6 to ensure peeling of the film 7 and peeling of the film 4. Peeling of the film 7 is exerted by delamination relative to the skin, the adhesive then exfoliating the skin with which it was in contact. Part of the skin is thus exfoliated and is positioned vertically to the substance 3 now uncovered. The user only has to place the patch against the skin with the palm of the hand, so that the substance 3 makes contact with the surface of exfoliated skin.

The relative positioning of the exfoliated skin and of the substance 3 is thus particularly precise and requires only reduced handling by the user. Also, the structure of the patch guarantees that the substance 3 will be well applied to a previously exfoliated skin.

Figure 4:
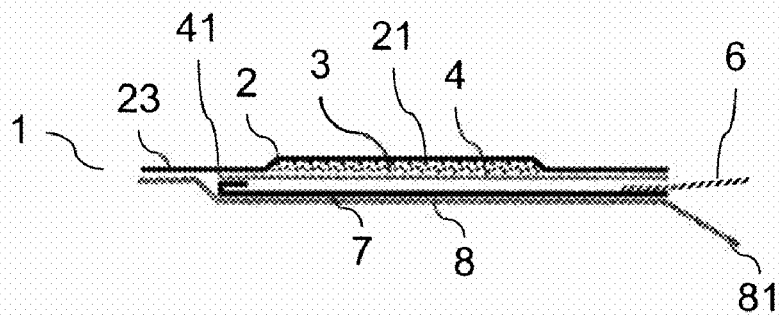
FIG. 4 is sectional view of a second embodiment of a patch according to the invention.

FIG. 4 illustrates a patch 1 according to a second embodiment. This patch 1 comprises a support 2 and a substance 3 similar to those of the first embodiment. A film 4 covers the substance 3 and keeps it in contact with the surface 21. The film 4 is peelable and thus fixed removably to the support 2. As in the first embodiment, the film 4 does not cover the adhesive part 23 of the support 2. The adhesive part 23 protrudes laterally relative to an end 41 of the film 4.

A peelable cutaneous exfoliation film 7 is attached to the film 4 by any appropriate means (adhesion, welding . . . ). As in the first embodiment, the film 7 is provided with a lower face having an adhesive surface. This adhesive surface is placed vertically to the substance 3. One end of the film 7 is fixed to the end 41 of the film 4. A prehension element 6 is fixed at the level of the opposite end of the film 7. The prehension element 6 projects laterally relative to the support 2.

A peelable protective film 8 covers the adhesive part 23 and the lower face of the film 7. The peelable film 8 also has a prehension zone 81, protruding laterally relative to the support 2, on the same side as the prehension element.

Figure 5:
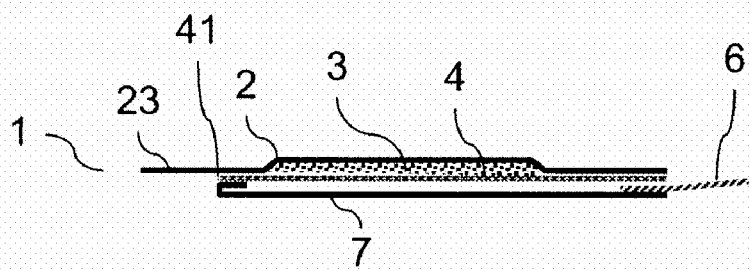
FIGS. 5 to 8 are sectional views of the patch of FIG. 4 during different steps of being placed onto the skin.
Figure 6:
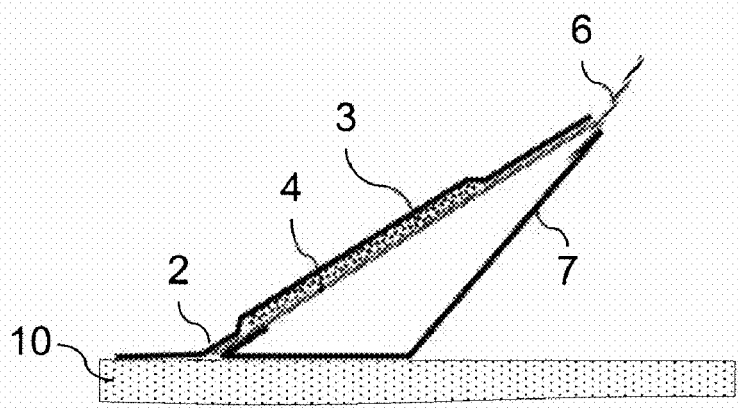
Figure 7:
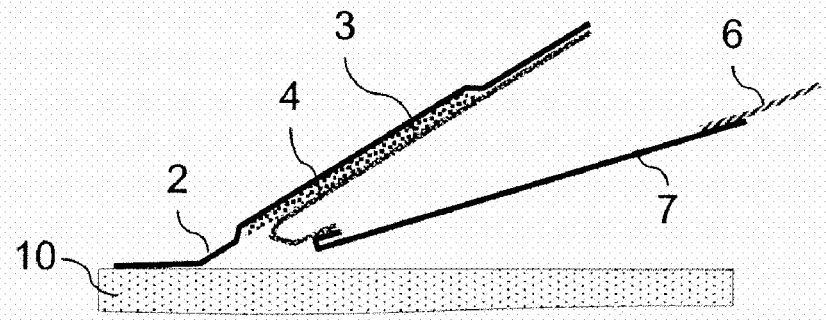
Figure 8:
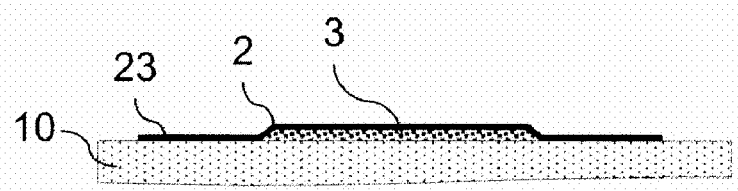

FIGS. 5 to 8 illustrate an application process for the patch 1 to the skin 10 of a user. In FIG. 5, the user has peeled the film 8, to expose the adhesive part 23 and the adhesive surface of the film 7. In FIG. 6, these adhesive surfaces have been placed in contact with the skin. By exerting traction upwards on the prehension element 6, the film 7 is delaminated from the skin and executes its exfoliating effect. In FIG. 7, the film 7 is fully delaminated from the skin. As the film 7 is attached to the end 41 of the film 4, it is likewise pulled along and is peeled relative to the support 2. The substance 3 is then uncovered and is positioned vertically to the surface of exfoliated skin. The user only has to place the patch 1 against the skin with the palm of the hand for the substance 3 to make contact with the surface of exfoliated skin, as illustrated in FIG. 8.

Figure 9:
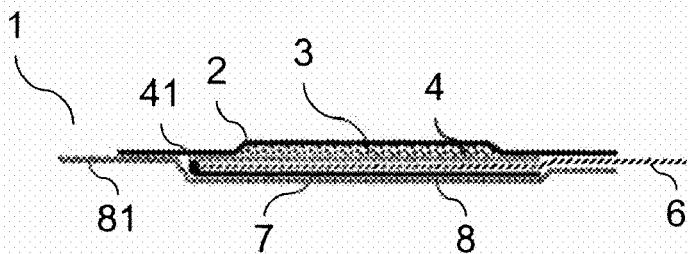
FIG. 9 is a sectional view of a third embodiment of a patch according to the invention.
Figure 10:
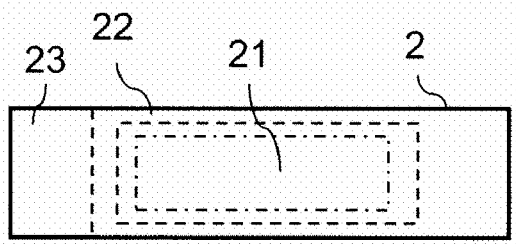
FIG. 10 is a plan view of each of the elements of the patch of FIG. 9.

FIGS. 9 and 10 illustrate a third embodiment of a patch 1. This patch 1 comprises a support 2 and a substance 3 similar to those of the preceding embodiments.

A film 4 covers the substance 3 and keeps it in contact with the surface 21. The film 4 is peelable and thus fixed removably to the support 2. As in the preceding embodiments, the film 4 does not cover the adhesive part 23 of the support 2. The adhesive part 23 projects laterally relative to an end 41 of the film 4. The film 4 is in contact with part of the adhesive surface 22 over the entire periphery of the surface 21. The peelable connection of the film 4 with the support 2 is assured by its contact with the adhesive surface 22. The film 4 is likewise surrounded by another part of the adhesive surface 22 which it does not cover. This other part is intended to come into contact with the skin and enclose the zone of exfoliated skin.

A peelable cutaneous exfoliation film 7 has an end fixed to the end 41 of the film 4. As in the preceding embodiments, the film 7 is provided with a lower face having an adhesive surface. This adhesive surface is placed vertically to the substance 3. As illustrated in FIG. 10, the film 7 has a form identical to the film 4.

A prehension element 6 made in the form of film is interleaved between the films 4 and 7. The prehension element is thus in contact with the films 4 and 7 by its two faces. This prehension element 6 has an end fixed to the end 41 of the film 4. The end opposite the prehension element 6 projects laterally relative to the support 2. The two faces of the prehension element 6 are partially coated with adhesive at the level of the contact surface with the films 4 and 7. These faces thus have adhesive strips 61 alternating with zones not coated with adhesive. These partially coated faces at the same time guarantee mechanical performance of the patch prior to use, while allowing delaminating of these faces relative to the films 4 and 7. The adhesive power must be sufficiently weak to allow delaminating when the user exerts traction on the prehension element 6.

A peelable protective film 8 covers the adhesive part 23 and the lower face of the film 7. The peelable film 8 also has a prehension zone 81, protruding laterally relative to the adhesive part 23 of the support 2.

When a user wants to apply the patch 1, he proceeds as follows: he peels the film 8, applies the adhesive of the exfoliating film 7 to the skin and places the adhesive surface 23 onto the skin. Because the respective ends of the films 4 and 7 and of the prehension element 6 are joined together, when the user exerts traction on the prehension element 6, it causes simultaneous peeling of the films 4 and 7. Part of the skin is thus exfoliated and is positioned vertically to the substance 3 now uncovered. The user only has to place the patch against the skin with the palm of the hand for the substance 3 to make contact with the surface of exfoliated skin.

Also, during peeling of the films 4 and 7, the lower adhesive face of the film 7 comes into contact with the surface of the film 4, which keeps the substance in the retention volume. Accordingly, any possible residue of the substance on the film 4 is neutralised.

Figure 11:
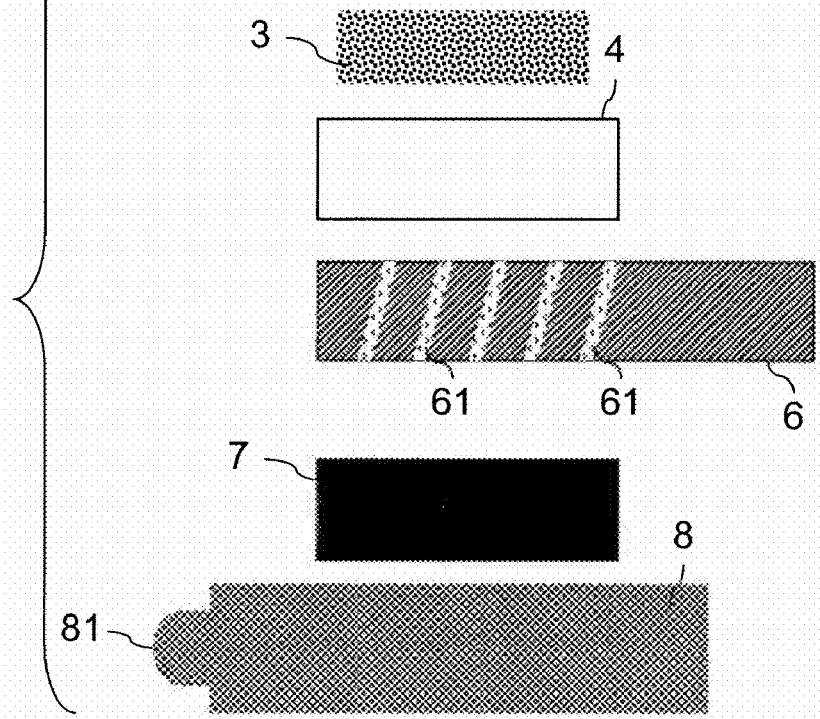
FIG. 11 is a lateral section of a fourth embodiment of a patch according to the invention.
Figure 11:
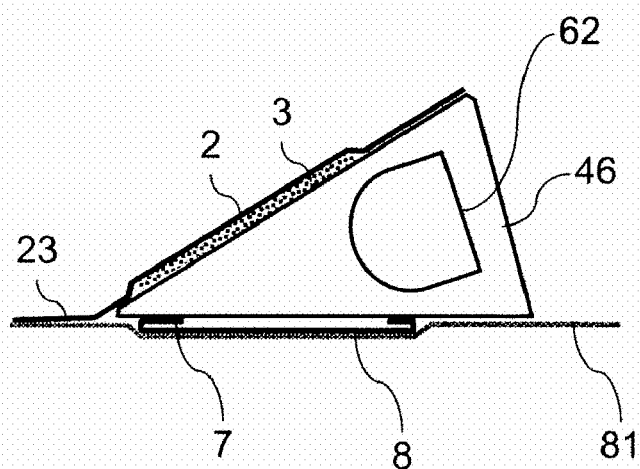

FIG. 11 illustrates a fourth embodiment of a patch 1. This patch 1 comprises a support 2 and a substance 3 similar to those of the preceding embodiments. An applicator 46 is used as removable means to keep the substance 3 in contact with the surface 21 prior to its cutaneous application. Also, the applicator 46 is likewise utilised as prehension element. The applicator 46 is thus in the form of a solid projecting perpendicularly relative to the lower face of the support 2. The applicator 46 has an overall form of a prism of triangular cross-section, whereof the bases are advantageously fitted with prehension indents 62 for the fingers of the user. A lateral face of the prism covers the surface 21 and keeps the substance 3 in contact with this surface 21. This lateral face will advantageously have weak adherence so that it can be easily separated from the support 2. This lateral face does not cover the part 23 of the surface 22.

A peelable cutaneous exfoliation film 7 has an end fixed to another lateral face of the prism. The other end of the film 7 is linked removably or breakably to this other surface of the prism. As in the preceding embodiments, the film 7 is provided with a lower face having an adhesive surface. This adhesive surface is placed vertically to the substance 3. A peelable protective film 8 covers the part 23 and the lower face of the film 7.

When a user wants to apply the patch 1, he proceeds as follows: he removes the peelable protective film 8, then applies the part 23 and the lower face of the film 7 against the skin. Lifting the rear part of the applicator 46 (opposite the part 23 of the support 2) breaks the breakable connection of one end of the film 7 with the applicator 46. Exerting traction on the applicator 46 uncovers the substance 3 and delaminates the film 7 from the skin. The applicator in effect peels the film 7 by pulling the front end to which it is fixed. As the palm of the hand is passed over the upper face of the support, the substance 3 is applied against the skin which has just now been exfoliated.

A protective film between the applicator 46 and the support 2 to keep the substance 3 against the surface 21 is likewise feasible. Such a protective film can be made in the form of a silicon film. This protective film can be installed peelable on the support 2 and have a front end fixed to the applicator 46. During traction of the applicator 46 this protective film will then be peeled.

In these different embodiments, it can be provided that the surface 21 exhibits electrostatic properties. It can then be provided that a substance 3 in the form of particles be kept in contact with the surface 21 by electrostatic forces.

Due to association of the substance 3 and an exfoliating film 7 vertically to this substance, the adhesive power of the film 7 can advantageously be calibrated as a function of the substance 3 or of its dosage.

The invention likewise relates to the use of a patch such as defined above for delivering molecules to the organism. The patch can especially be utilised for vaccination of subjects, for desensitising subjects, or for delivering any active substance. The active substances contained in the patch can be any kind, preferably polypeptidic, and can be biologically active compounds or antigens, for example.

What is claimed is:

1. A patch for cutaneous application of a substance, characterised in that it comprises
   a substance intended to penetrate the epidermis,
   means for contacting the substance with the skin, and
   a cutaneous exfoliation peelable film allowing exfoliation of the skin, after the patch has been put into place, at the level of the contact zone between said substance and the skin.

2. A patch as claimed in claim 1, characterised in that it comprises:
   a support comprising at least one lower face having a first surface in contact with said substance and a second surface intended to make contact with the skin;
   removable means maintaining the substance in contact with said first surface;
   the cutaneous peelable exfoliation film being attached to the support and comprising a lower face having an adhesive surface placed vertically to said substance; and
   means for keeping the second surface in contact with the skin when the exfoliation film has been peeled.

3. The patch of claim 2, in which the second surface is adhesive and encloses the first surface (21).

4. The patch of claim 2, in which the removable means for keeping the first surface in contact with the substance comprise a protective element interposed between the exfoliation film and the support, the protective element covering the first surface.

5. The patch of claim 4, in which the means for keeping the second surface and the substance in contact with the skin comprise an adhesive coating the second surface, and in which the second surface has a portion non-covered by the protective element.

6. The patch of claim 5, comprising a peelable protective film covering and in contact with said non-covered portion and with the lower face of the exfoliation film.

7. The patch of claim 2, comprising a prehension element projecting relative to the support, the prehension element being attached to the exfoliation film so as to delaminate the exfoliation film from the skin when the prehension element is handled.

8. The patch of claim 7, in which the prehension part projects laterally relative to the support, to the side opposite the portion non-covered by the protective element.

9. The patch of claim 7, in which the prehension element is attached to the removable means, such that these removable means are withdrawn when the prehension element is actuated.

10. The patch of claim 9, in which the exfoliation film and the removable means are attached by respective first ends.

11. The patch of claim 10, in which the prehension element is attached to a second end of the exfoliation film or the removable means, this second end being opposite the first.

12. The patch of claim 10, in which the removable means comprise a film, and in which the prehension element comprises a film in contact with the film of the removable means and with the upper surface of the exfoliation film via faces partially coated with adhesive.

13. The patch of claim 7, in which the removable means and the prehension element comprise a folded film.

14. The patch of claim 7, in which the prehension element is folded back and attached removably on the upper surface of the support.

15. The patch of claim 7, in which the prehension element projects perpendicularly to the lower face of the support.

16. The patch of claim 15, in which the removable means and the prehension element comprise an element in the form of a prism of triangular cross-section having bases with prehension indents, a lateral face covering the first surface, and another lateral face attached to at least one end of the exfoliation film.

17. The patch of claim 2, in which the support and the removable means maintain the substance in a volume of hermetic retention.

18. The patch of claim 2, in which the first surface has electrostatic properties and in which the substance comprises particles maintained in contact with the surface by electrostatic forces of the type of Coulomb or van der Waals forces.

19. The patch of claim 2, in which the adhesive power of the adhesive surface of the exfoliation film is calibrated as a function of the substance.

* * * * *